US006818003B2

(12) United States Patent
Genovesi

(10) Patent No.: US 6,818,003 B2
(45) Date of Patent: Nov. 16, 2004

(54) BLOOD VESSEL HARVESTING DEVICE

(76) Inventor: Mark H. Genovesi, 295 Central Park West (Apt 14F), New York, NY (US) 10024

(*) Notice: Subject to any disclaimer, the term of this patent is extended or adjusted under 35 U.S.C. 154(b) by 3 days.

(21) Appl. No.: 10/345,739

(22) Filed: Jan. 16, 2003

(65) Prior Publication Data
US 2004/0143279 A1 Jul. 22, 2004

(51) Int. Cl.[7] .................................... A61B 17/22
(52) U.S. Cl. ........................ 606/159; 600/114
(58) Field of Search .............. 606/110, 113, 606/46, 47, 48, 159, 158, 170, 180, 190; 604/22; 600/114, 104, 210, 212, 235

(56) References Cited

U.S. PATENT DOCUMENTS

| 4,793,346 A | * 12/1988 | Mindich | 606/28 |
| 5,358,485 A | * 10/1994 | Vance et al. | 604/22 |
| 5,373,840 A | 12/1994 | Knighton | |
| 5,448,990 A | * 9/1995 | De Faria-Correa | 600/129 |
| 5,556,405 A | * 9/1996 | Lary | 606/159 |
| 5,667,480 A | * 9/1997 | Knight et al. | 600/210 |
| 5,899,912 A | 5/1999 | Eaves, III | |
| 5,922,004 A | 7/1999 | DuBois | |
| 6,036,713 A | 3/2000 | Kierurakis | |
| 6,042,538 A | * 3/2000 | Puskas | 600/114 |
| 6,143,008 A | 11/2000 | Eaves, III | |
| 6,193,653 B1 | 2/2001 | Evans | |
| 6,206,899 B1 | 3/2001 | Ginn | |
| 6,277,137 B1 | * 8/2001 | Chin | 606/190 |

FOREIGN PATENT DOCUMENTS

WO        WO 99/25238        5/1999

* cited by examiner

Primary Examiner—Julian W. Woo
Assistant Examiner—Victor Nguyen
(74) Attorney, Agent, or Firm—Richard L. Strauss, Esq.

(57) ABSTRACT

A method and device are disclosed directed at harvesting of vessels, such as arteries and veins, especially as required in vessel grafting procedures. The device and method discloses a cannula-like device that provides identification, capture, manipulation, cautery and cleavage of branch vessels from the harvested vessel. In certain preferred embodiments of the disclosed method and device, irrigants containing $CO_2$, as well as other agents capable of stimulate release of nitric oxide from vascular endothelium are applied to subject vessels so as to enhance the viability of vessels to be harvested as graft material.

53 Claims, 6 Drawing Sheets

BLOOD VESSEL HARVESTING DEVICE

TECHNICAL FIELD

The present invention is related to devices and methods of utilizing such devices for harvesting blood vessels. More specifically, the present invention is directed at a device and method particularly useful in separating a desired artery or vein from lateral branch vessels so as to allow excision of such for use as, for example, a graft.

BACKGROUND OF THE INVENTION

It is a fairly common procedure to utilize viable healthy blood vessels from one part of a patient's circulatory system as a graft in order to replaced a blocked, damaged or diseased vessel at another location. For example, the coronary arteries are especially prone and subject to atherosclerosis as well as other vessel damaging and occluding diseases. Coronary bypass surgery commonly utilizes healthy segments of the radial artery, saphenous vein and other blood vessels as grafts to replace such diseased vessels.

In order to obtain a suitable length of a given artery or vein for use as a graft, a harvesting procedure in which a surgeon excises a desired length of donor vessel must first be accomplished. In accomplishing such harvesting procedures, the selected donor vessel must be safely separated from lateral (or branch) vessels arising from the main vessel to be harvested. Also, the donor vessel must be cleaved, at a proximal and distal point from them main vessel from which it arises in order to fully free the segment for use as a graft.

Harvesting procedures involve obtaining access to the donor vessel. In the past, such access has been accomplished with lengthy skin incisions made along the length of vessel to be harvested. Thereafter, blunt dissection of the vessel from connective tissue, fat and other structures adherent upon it, followed by cleavage of branch vessels was commonly performed. Recently, endoscopic approaches have been utilized to harvest vessels. Such procedures typically commence with small skin incisions made at locations in close proximity to the proximal and distal extent of the graft desired are first made. Thereafter, an endoscope is utilized along with instruments, especially designed for endoscopic surgery, to accomplish blunt dissection and severing of the vessel from lateral branches. Such techniques are far more conservative in nature and involve substantially reduced skin incisions—and concomitant prolonged healing and pain—as compared to open techniques. However, the relatively small enclosed field in which multiple instruments must be utilized makes the procedure somewhat less than ideal. U.S. Pat. No. 5,899,912, Eaves III (the "'912 patent") discloses a harvesting apparatus utilized in endoscopic removal of blood vessels. The disclosed harvesting instrument includes a harvesting head with a channel for receiving a blood vessel as well as at least one slot extending from the channel to the outer surface of the harvesting head for receipt of side branches of the vessel. The slot contains a blade for severing side branches and electro cautery for sealing the cut ends of the vessel. The outside surface of the harvesting head may be utilized for blunt dissection about the vessel to be harvested. Although the '912 patent discloses a harvesting instrument which provides blunt dissection as well as cleavage and sealing of side branches, the device does not provide any means of operator control or guidance of the position of vessels within the harvesting head save through the gross manipulation of a handle depending from the harvesting head. Also, no means is disclosed for retaining a vessel within the instrument during the cufting/cautery procedure.

SUMMARY OF THE INVENTION

Now in accordance with the present invention, a blood vessel harvesting device is disclosed. The harvesting device of the present invention is comprised of a harvesting cannula generally configured as an elongated, hollow tube having a longitudinal axis. The cannula includes an outer wall, a central bore, a proximal and a distal terminus. The cannula is comprised of three sections: a harvesting head, a tubular control segment and a sliding operation arm. The tubular control segment and harvesting head are contiguous structures which form a portion of the hollow, tubular cannula structure discussed above.

The tubular control segment is located and forms, in combination with a proximal portion of the sliding operation arm, the proximal portion of the harvesting cannula. The control segment joins distally and is continuous with the harvesting head which is located at the distal end of the cannula. The sliding operation arm is slidably affixed and completes a superior portion of the outer walls of both the control segment and harvesting head. The outer walls of the harvesting head, tubular control segment, and sliding operation arm define the elongated, hollow harvesting cannula and surround, so as to form the central bore there within.

As mentioned above, when positioned in a forward (or fore) position, the distal terminus of the sliding operation arm comes into contact with and completes a superior aspect of the distal portion of the outer wall of the harvesting head. When positioned in a rearward or aft position, a space is formed between the harvesting head and sliding operation arm so as to form the lateral branch capture notch, discussed below. Therefore, in the fore position, the sliding operation arm provides completion of the outer cannula walls save for the main vessel alignment slot, discussed below. The term "aft", as utilized throughout this specification and in the claims is a directional term which refers to the proximal end of the cannula. Thus, the term "aft direction" means towards the proximal end of the cannula. The term "fore", as utilized throughout this specification and in the claims is a directional term referring to the refers to the distal end of the cannula. Thus the term "fore direction" means towards the distal end of the cannula.

The harvesting head, located at and forming the distal portion of the cannula includes a central bore, proximal and distal terminus, and may be described as including superior and inferior portions. The harvesting head may advantageously include an opening (or "distal aperture") at the distal terminus thereof (which is also the distal terminus of the entire device). The distal aperture is contiguous with the central bore of the cannula.

The outer wall of the harvesting head is interrupted by a main vessel alignment slot penetrating through the outer wall of both the harvesting head and the distal portion of the sliding operation arm (which, in a fore position, completes the proximal extent of the superior outer wall of the harvesting head). The alignment slot communicates freely with the central bore. The main vessel alignment slot may be advantageously configured at an angular (non-parallel) relation with the longitudinal axis of the cannula so as to assist vessel retention as discussed below. The slot extends from the distal terminus of the cannula (distal terminus of the harvesting head) proximally and terminates in the proximal/superior portion of the outer wall of the harvesting head completed by the sliding operation arm.

The specific width and length of the main vessel alignment slot is configured so as to provide—as discussed below—efficient capture and retention of vessels to be harvested. Retention of the vessel to be harvested is aided by both the skewed position of the main alignment slot—in embodiments incorporating such configuration—as well as engagement of the vessel by the vessel capture and manipulation means or, in certain alternative embodiments, the main vessel retention gate(s), discussed below.

In preferred embodiments of the present invention, the distal portion of the cannula comprising the harvesting head exhibits a greater diameter relative to the remainder of the cannula. Increased diameter provides an increased central bore area for accommodating branch arteries, increasing the operative field thereby enhancing visualization of the procedure and providing more area for manipulation of vessels (as discussed below). Also, in certain preferred embodiments of the present invention, the harvesting head may be advantageously shaped and configured in an elliptical (or "egg shape") with tapered proximal and distal termini in order to aid blunt dissection about the vessel to be harvested. In addition to the increased visualization provided by the enlarged central bore of the harvesting head, it is preferred that embodiments of the present invention are comprised of a biocompatible transparent material such as, for example a plastic material so as to further enhance visualization of the operative field. It is also preferred that the material of which the cannula is comprised is non-conduction so as to facilitate safe use of electro and radio surgical instruments as described herein.

The proximal portion of the cannula—the tubular control segment—provides a means of positioning the harvesting head (e.g. a handle) as well as a conduit for passage of various linkages, tubes and wires to the distal end of the instrument. Therefore certain preferred embodiments of the present invention may advantageously include a plurality of apertures at the proximal terminus and/or channels through the outer wall of the control segment so as to provide access for instrument control cables, rods, lines and linkages in order to provide, for example: irrigation, with or without $CO_2$ aspiration; endoscopic cameras, lighting and the below described vessel capture/manipulation means. Such cables, lines, rods and linkages may, as described below, be positioned within the central bore of the cannula or be housed within channels located within the outer walls thereof.

The outer wall of the harvesting head includes, in addition to the main vessel alignment slot, at least one branch vessel capture notch penetrating through to the central bore. The at least one branch vessel capture notch is positioned so as to extend laterally from the main vessel alignment slot near to the proximal extent and portion of the main alignment slot. The branch vessel capture notch can also be described as running, from a distal portion of the main alignment slot, in a generally circumferential direction about the longitudinal axis of the cannula along the outer wall of the harvesting head. The capture notch freely communicates with the vessel alignment slot as well as the central bore of the harvesting head. Positioning the branch vessel capture notch(es) adjacent the distal portion of the alignment slot enhances the effect of biasing forces, applied by vessel retention means, which assist guidance and seating of branch vessels within the capture notch(es) (discussed below).

In the first preferred embodiment of the present invention, the capture notch(es) is defined and formed between edges of the outer walls of the sliding operation arm and harvesting head. For example the capture notch may be formed by and between 1. an edge of the outer wall comprising the distal terminus of the sliding operation arm; and 2. an adjacent edge of the outer wall of a superior portion of the harvesting head adjacent to the distal terminus of the sliding operation arm. In a "closed" position in which the sliding operation arm is in a "fore" position, these adjacent edges of the sliding operation arm and harvesting head are in contact and, in fact, the distal portion of the sliding operation arm completes the superior aspect of the harvesting head in such a configuration. In an "open" position, a space or "notch" forms between the afore-mentioned superior portion of the harvesting head and sliding operation arm so as to form the capture notch(es). More specifically, in an "aft" position, the sliding operation arm is moved backwards by a surgeon, so as to leave a gap between the outer wall (and the edges of the walls defining the termini thereof of the sliding operation arm and the edge of the outer wall of the harvesting head ordinarily adjacent and in opposition thereto. This gap—the branch vessel capture notch—is advantageously utilized in preferred embodiments of the present invention to capture, apply hemostasis to, and sever branch vessels from the segment of the vessel to be harvested. The opposing edges of the outer wall of th harvesting head and sliding operation arm forming the capture notches may converge, to a slight extent, distally, in order the enhance positioning of a lateral vessel in proper alignment with cautery, cutting and/clipping means. In preferred embodiments of the present invention, the at least one branch vessel capture notch communicates with the main vessel alignment groove proximate to the grooves proximal terminus.

The afore-mentioned edges of the outer wall defining the at least one vessel capture notch of the present invention include a means for severing branch (also referred to as "lateral") vessels from the vessel to be harvested. The means for severing branch vessels may be selected to be, for example, bi-polar or uni-polar electro surgery cutting instruments (also referred to as electro or radio surgery/cautery "tips"), laser cutting instruments, harmonic instruments or cold steel (edged instruments). In addition, the notches may also be provided with electro-cautery means so as to enable coagulation (and hemostasis) of such branch vessels. The notches may also be equipped so as to apply surgical clips or coils such as, for example nitinol™ coils to vessels so as to avoid the creation of potentially injurious heat during cauterization. Thus, the device of the present invention contemplates, in certain preferred embodiments, 1. coagulating branch arteries by means of, for example, the use of electro surgery tips applying coagulating current; 2. applying surgical clips or coils to mechanically occlude branch vessels; 3. severing such branch arteries by means of electro surgery tips applying cutting current, laser means, ultrasonic means and cold steel for severing branch vessels; and 4. utilizing both coagulation (for hemostasis) or surgical clips/coils and cutting means.

In embodiments of the present invention wherein the at least one vessel capture notch is provided with both electro cautery (or coils/clips) for hemostasis as well as a severing means (such as electro surgical tips utilizing a cutting current, a laser means, harmonic means or cold steel), it is highly advantageous to position, for example, coagulating electro cautery tips (or coils) at two points along the branch vessel capture notch located on either side of the cutting means. In this way, as discussed in further detail below, branch vessels captured within the notch(es) may be coagulated or mechanically crimped (so as to provide hemostasis) on either side of the point at which the vessel is severed thereby reducing or eliminating blood loss during branch vessel release.

It is preferred that the device of the present invention includes two branch vessel capture notches located lateral to, and on opposite sides of the main vessel alignment slot. The branch vessel capture notch(es) are advantageously positioned, for example, lateral to the alignment slot, between the below described main vessel capturing means and the distal terminus of the slot. Such positioning, as discussed below, improves the ease with which the device may engage vessels to be harvested while taking advantage of the biasing force provided by the main vessel capturing and manipulation means (discussed below) and/or main vessel capture gate utilized to guide the branch vessels into the capture notches.

It is highly advantageous, in certain preferred embodiments of the present invention, to configure the harvesting cannula so as to include, at an inferior portion thereof, a concave segment of outer wall located generally opposite the main vessel alignment slot—bulging outward, away from the central slot—so as to provide, as discussed in more detail below, adequate room within the central bore for branch vessels arising from a posterior portion of the vessel to be harvested. Such a configuration allows the cannula to pass along the main vessel and engage lateral branch arteries, without being stopped or hindered by posterior branches. After severing lateral branches in the vicinity of such bulges, the main vessel capture/manipulation means may be utilized with or without rotation of the entire cannula, so as to allow the at least one capture notch to engage and then sever such posterior branches.

The harvesting cannula of the present invention includes a means for retaining the vessel to be harvested within the harvesting head—separate and apart, for example, from the skewed configuration of the main vessel alignment slot—discussed above. The retaining means provides two functions. Firstly, the retaining means acts to simply maintain the main vessel within the confines of the central bore of the harvesting head. Secondly, the retaining means creates a biasing force that assists the surgeon in capturing and positioning branch vessels within the branch vessel capture notches. If the retaining means is, in fact, a capture and manipulation means, then a third function, enhanced manipulation of side branches into the capture notch(es), is provided.

In a first preferred embodiment of the present invention, a main vessel capture and manipulation means is provided so as to allow capture and retention of a vessel to be harvested within the central bore of the harvesting head; and 2. manipulation of the vessel in lateral, superior and inferior directions so as to assist positioning of branch vessels within branch vessel capture notches. The main vessel capture and manipulation means may be advantageously comprised of, for example, a control rod running through the control segment and/or sliding operation arm to the central bore of the harvesting head. A proximal terminus of the control rod is linked to a control means enabling an operator to rotate and, in certain preferred embodiment, control fore/aft movement of a distal, vessel engaging terminus of the rod. For example, the distal terminus of the control rod may be advantageously configured to include, for example, a "V" or "L" shaped bend for vessel entrapment and control of movement. In certain other preferred embodiments, the distal terminus of the control rod may include a coiled configuration. For example, a "pig tail" may be provided at the distal terminus of the control rod so as to allow capture and manipulation of a vessel to be harvested. The vessel engaging terminus is positioned so as to allow and provide capture of the main vessel in close proximity to the proximal terminus of the main vessel alignment slot. For example, the engaging terminus may be advantageously positioned just proximal to the branch vessel capture notches. Such positioning allows the control rod to apply sufficient downward (towards the inferior surface of the cannula and harvesting head) biasing forces upon a main vessel captured within the central bore so as to cause branch arteries to drop into the capture notches. Therefore, in the first preferred embodiment of the present invention, the harvesting cannula incorporates a vessel capture/manipulation means in order to provide a surgeon with a means of controlling the lateral as well as superior/inferior position of a vessel to be harvested—and the branch vessels thereof—so as to enable: a. capture and retention of a portion of the main vessel within the central bore of the cannula; and 2. manipulation of the vessel so as to guide branch (lateral and posterior) vessels into capture notches for severance and hemostasis (coagulation/surgical clip) procedures. For example, in embodiment of the present invention wherein the capture and retention means comprises a control rod, the distal terminus (the vessel engagement configuration) may be configured as an open coil. In such configuration a proximal control means such as, for example, a sliding dial, may be used to advance the coil towards the main vessel, rotate the coil to an open position to engage the vessel, and then further rotate the coil for vessel capture. Thereafter the control rod is utilized to manipulate the main vessel (the vessel to be harvested) in such a manner as to cause branch vessels to enter and be properly positioned within the branch vessel capture notches. The term "properly positioned" as used herein in regard to control rod manipulation of branch vessels refers to placement of the branch vessels at a position within the slot notches wherein the vessel is aligned with vessel coagulation means, cutting means and/or clip application means.

In a second preferred embodiment of the present invention, the main vessel retaining means comprises a retention gate positioned just distal to the proximal terminus of the main vessel alignment slot. The man retention gate is positioned a sufficient distance, as described below, so as to allow enough clearance for the main vessel to exit the cannula between the gate(s) and the proximal slot terminus. The retention gate may be comprised of one gate or two gates which are operably positioned in either 1. an "open" position leaving the main alignment slot unobstructed for initial vessel capture and 2. a closed position wherein the gate(s) breach the width of the main alignment slot, just forward (fore) of the distal terminus thereof so as to allow capture of a vessel to be harvested within the device. As in the case of the vessel capture/manipulation means, the retention gate, positioned just forward of a vessel exiting the cannula (at the proximal terminus of the alignment slot) creates a biasing force so as to urge the main vessel (as branch vessels attached thereto) downward, thereby aiding capture of lateral vessels within the capture notches.

The harvesting cannula of the present invention also advantageously includes, or provided means for including an endoscopic camera within the confines thereof for visualizing the vessel to be harvested as well as the aforementioned manipulation/coagulation and cutting of branch vessels. In addition, certain preferred embodiments of the present invention incorporate a means for irrigating the operative field with, for example, saline solution and $CO_2$ within the cannula. Such irrigation may be provided by delivery lines entering the proximal terminus of cannula through various apertures. These lines may run, for example, through the central bore of the cannula or within channels inside the outer walls of the device. Irrigation supply lines may, for example, junction with apertures and jets at their distal terminus positioned so as to direct a stream of such liquids and gasses towards the lens of an endoscopic camera, clearing the operative field (the area of the notch(es) wherein branch arteries are severed/coagulated), and cleansing the central bore of the harvesting cannula.

In certain preferred embodiments of the present invention, the outer wall—and most advantageously the inferior aspect thereof—of the cannula includes perforations so as to allow such irrigation to exit the central bore of the cannula and form an aqueous layer or a carboxylated aqueous layer about the cannula enhancing the ease of manipulating said device. In addition, preferred embodiments of the present invention include a means for aspiration of the operative field and the area about the cannula. For example, in certain preferred embodiments of the present invention, the proximal terminus of the harvesting cannula provides a means, such as an aperture or suction fitting, so as to provide aspiration of the central bore of the device. In addition, perforations in the outer wall of the harvesting head allow such aspiration to be applied to, so as to evacuate naturally occurring operate site fluids (such as blood) as well as fluids utilized for irrigation about the surgical site.

The present invention also discloses a method of harvesting blood vessels utilizing the vessel harvesting device disclosed herein. In practicing the method of the present invention, a vessel to be harvested is first identified. Thereafter, and after the usual and appropriate surgical site disinfection/preparation and administration of anesthesia, a skin incision is made in the vicinity of the distal extent of the graft to be harvested. Thereafter, through careful blunt dissection, an area circumferentially about the subject vessel is freed proximally until the operative field about the most proximal extent of the graft desired is reached. Thereafter, the distal terminus of the harvesting cannula is introduced through the distal skin incision and positioned so that a portion of the vessel to be harvested—still fully connected to the circulation, both proximally and distally—enters the cannula through the distal aperture and/or vessel alignment slot. Thereafter, the main vessel capture and manipulation means is utilized, alone and in combination with gross cannula manipulation—to engage and capture the vessel to be harvested within the central bore of the cannula. In certain preferred embodiments of the present invention the harvesting cannula itself, as described below, may be utilized to perform some or all of the blunt dissection.

In embodiments of the present invention wherein branch vessel capture notches are provided and formed by and between the superior proximal terminus of the harvesting head and the distal terminus of the sliding operation arm, the sliding operation arm is first placed in an open (or aft position). More specifically, prior to branch vessel capture, the sliding operation arm is placed in an aft position so as to open access to the branch vessel capture notch formed by the space created between the sliding arm and the harvesting head. Thereafter, the cannula is advanced along the main vessel. The sliding operation arm may, from time to time and as needed, be opened (moved to a more aft position) and closed (moved to a more fore position) so as to facilitate capture and retention of branch vessels. Also, and as described in further detail below, in certain preferred embodiments of the present invention, vessel coagulation and cutting means can be operated by "closing" the capture notch by fore motion of the sliding operation arm.

As branch vessels are encountered and identified, the main vessel capture and manipulation means is utilized to bias the main vessel so as to urge branch arteries into a position within the capture notches. As discussed above, the location of the capture and manipulation means provides a downward, biasing force against the vessel so as to facilitate entry into the capture notch. The cannula may also be manipulated in a fore/aft as well as a rotating manner, so as to assist the vessel capturing/manipulating means in positioning the branch vessel adjacent the most distal extent (or distal terminus) of the capture notch opposite its origin at the alignment slot. Furthermore, in embodiments of the present invention wherein a retention gate(s) are utilized, such gate(s) also provide the same downward biasing force so as to facilitate lateral vessel capture and positioning within the notches. In certain preferred embodiments of the present invention, the concave portion of the outer cannula wall opposite the alignment slot provides room for branch arteries that may arise from the posterior of the vessel to be harvested and prevents such posterior vessels from interfering with cannula operation and advancement.

Thus positioned, the branch vessel is then separated from the main vessel after hemostasis by severing means such as, for example, electro surgery cutting tips, cutting blades, and/or a laser means located adjacent to the edges of the outer cannula wall defining the lateral edges of the capture notch. For example, opposite edges of the capture notch may be provided with bipolar electro surgery tips wherein one edge includes an operating (active) tip/contact and the opposite end an antenna (neutral/ground) tip/contact. In addition, it certain embodiments, it may be preferred to utilize unipolar cautery with a grounding plate. In other embodiments, it may be preferred to utilized cutting blades fabricated of, for example, surgical steel to free the main vessel to be harvested from the lateral branch captured within the notch. Furthermore, the notch may include a laser or harmonic (e.g.,ultrasonic) cutting means to remove the lateral branch. However, it is preferred that the at least one lateral branch capture notch includes electro surgery tip(s) capable of delivering coagulating current so as to allow homeostasis on either side of the site of branch vessel severing prior to such cleavage. Alternatively, surgical clips or coils can be applied at the capture notches to effect a similar hemostatic function. Certain embodiments of the present invention incorporate electro surgical tips, both bi-polar and uni-polar which provide both coagulating and cutting functions simply by altering the type of current (wave pattern) applied thereto.

It is still further preferred that two coagulation points be provided on either side of vessel severance by means of, for example, two pairs of electro cautery tips, positioned on either side of a cutting means centered there between. For example, two pairs of bi polar electro surgery tips/contacts (active and antenna/ground) may be positioned on opposite edges and adjacent to the lateral terminus of the capture notch. A cutting means, such as, for example, a remotely controlled cutting blade may be advantageously located between the two pairs of coagulating tips or, in certain preferred embodiments, fore motion of the sliding operation arm is utilized to urge the cutting blade through the vessel. Therefore, when a branch vessel is identified by the remote camera within the main vessel capture/manipulation means may be utilized so as to bias the lateral branch into the capture notch adjacent to the cutting and hemostatic means therein. (Utilizing embodiments of the present invention comprised of non-conductive transparent plastic greatly facilitates such visualization). The capture/manipulation means is utilized to accurately position the branch arteries precisely at the correct cutting point. Thereafter two coagulation points, effectively occluding the vessels are made close to its junction with the vessel to be harvested. Alternatively, the device may be utilized to place surgical clips on either side of the cutting point for hemostasis. The cutting blade is then operated so as to cleave the branch vessel from the subject graft. Thus, the vessel is severed only after hemostasis is achieved. In certain preferred embodiments of the present invention, fore motion (or closure) of the sliding operation arm may be utilized to effect the afore-mentioned severing of branch vessels (as described in further detail, below).

After each branch vessel is removed from the main vessel, as described above, the cannula is advanced along the vessel, towards the proximal extent of the graft desired, capturing, coagulating (or clamping, e.g. nitinol™ coils) and cleaving further branch vessels as they are encountered in a like manner. Irrigation, delivered within the cannula and directed upon the surgical site where said cutting and coagulation are performed maintains a clear operative field. Furthermore, irrigant flow upon the lens of the camera is provided to keep same free of obstructions. The cannula may be provided with a multiplicity of perforations through the external wall, so as to provide further application of irrigant about the device so as to aid ease of manipulation as well as visualization. The cannula may also be provided with a suction means within the cental bore so as to removed irrigant, blood and debris from the operative site.

In certain preferred embodiments of the method of the present invention, a gaseous stream of $CO_2$, is combined with fluid irrigant such as, for example, a saline solution. The inclusion of $CO_2$, has now been found to have significant effects upon the release of Nitric Oxide (NO) from the vascular endothelium. Therefore, inclusion of agents that may either enhance or diminish the release or production of Nitric Oxide may be added to, for example, a mister blower for application to the surgical site and the subject vessel to be harvested. More specifically, it has been found that the controlled release of Nitric Oxide, tends to relax the endothelial lining and thereby significantly increased the viability of such vessels for use in grafting procedures such as, for example, coronary artery bypass. More specifically, it has now been discovered that by incorporating a flow of form about 2 L/Min (liters/minute) to about 4 L/Min $CO_2$ the irrigant flow, a maximum beneficial effect is provided.

Upon coagulation and separation of all branch vessels which junction with the desired length of vessel to be harvested, a second skin incision may be made in the vicinity of the proximal extent of the graft. The proximal vessel transection may be made with the harvesting device, without need for a second incision. Alternatively, the vessel may be clipped or coagulated via an endoscopic procedure, without the use of a second incision prior to transection. Thereafter, the vessel is separated at its proximal and distal extent by the usual means.

Upon coagulation and separation of all branch vessels which junction with the desired length of vessel to be harvested, a second skin incision is made in the vicinity of the proximal extent of the graft. Thereafter, the vessel is separated at is proximal and distal extent by the usual means.

DETAILED DESCRIPTION

Figure 1:
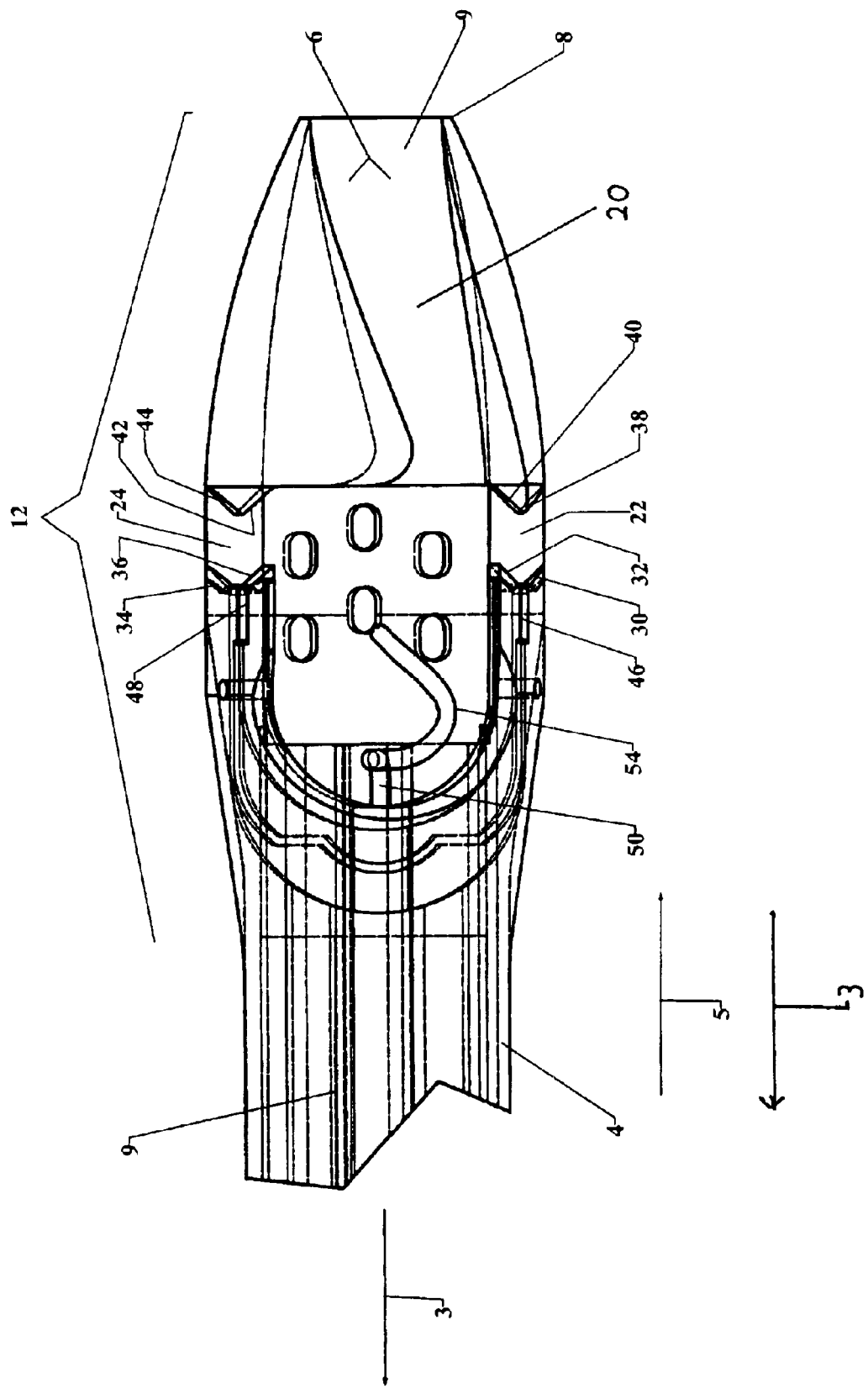
FIG. 1 is a top view of a portion of a preferred embodiment of the present invention.
Figure 2:
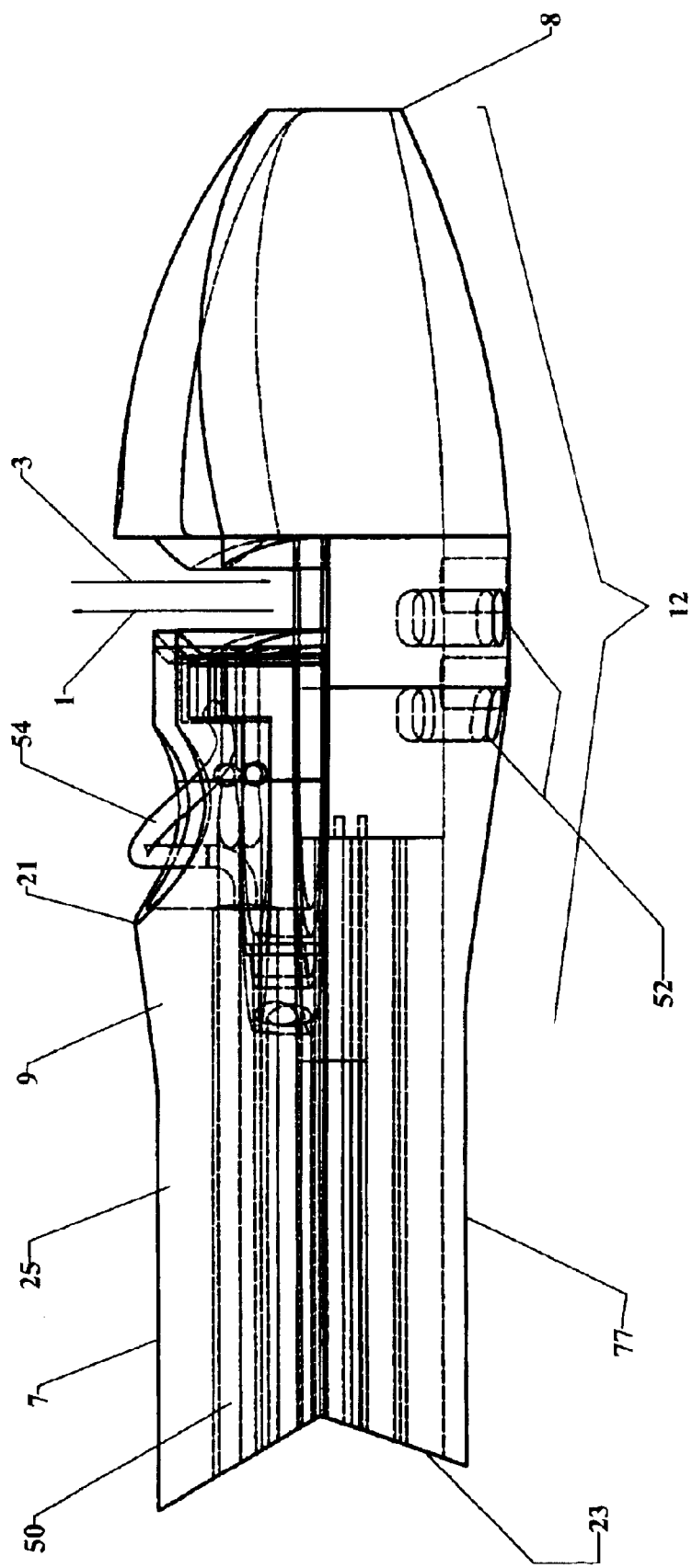
FIG. 2 is a lateral view of the preferred embodiment illustrated in FIG. 1.
Figure 3:
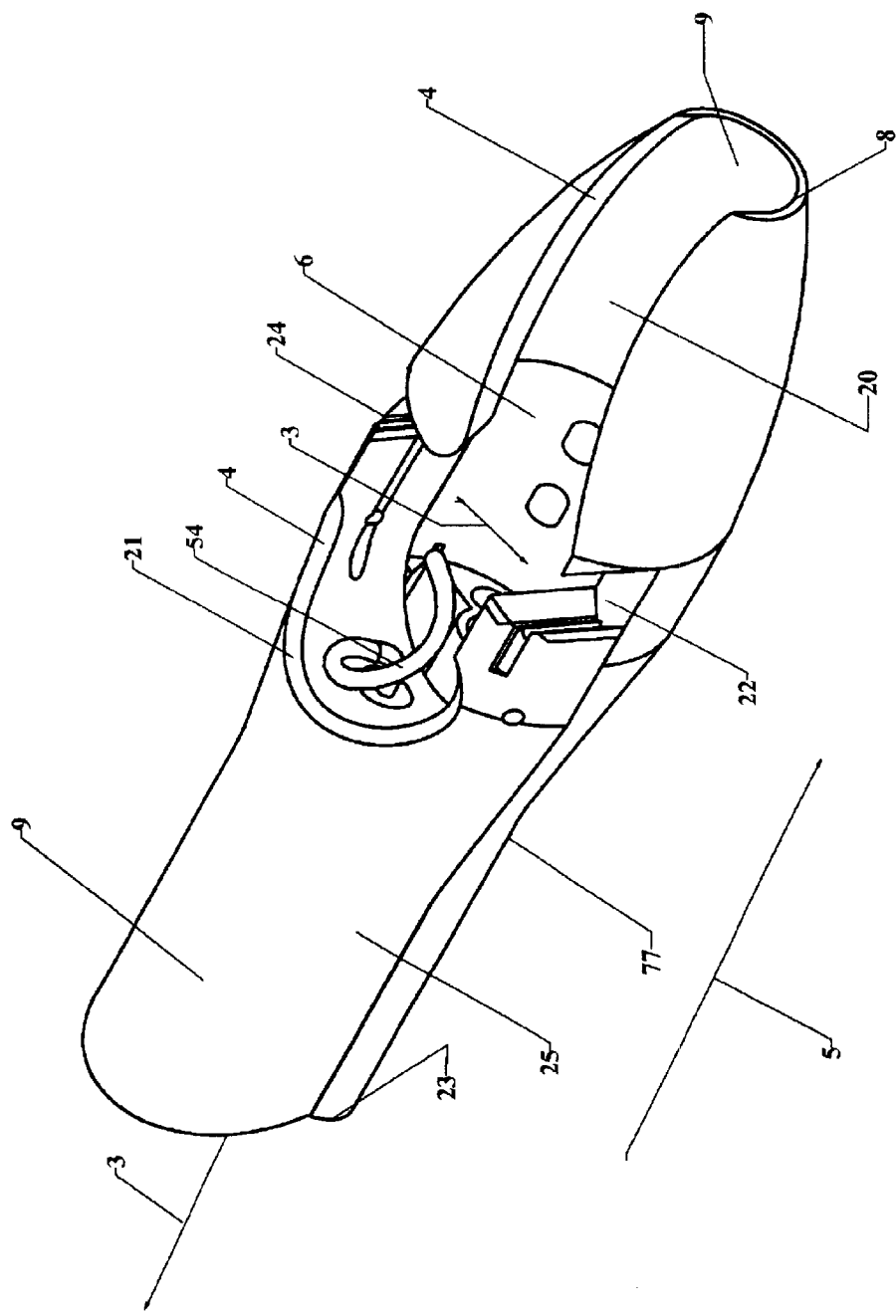
FIG. 3 is a front lateral view of the preferred embodiment illustrated in FIG. 1.

FIGS. 1–5 illustrate a harvesting cannula in accordance with a first preferred embodiment of the present invention. Harvesting cannula 2 is configured as an elongated, hollow, tubular structure. It is preferred that the cannula is fabricated of a transparent, biocompatible, non-conductive material such as, for example, a plastic. The cannula has an outer wall 4, a central bore 6, a distal terminus 8, a proximal terminus 10 and a longitudinal axis running from the proximal to distal terminus. Located adjacent the distal terminus, a harvesting head 12 exhibits a greater diameter relative to the remainder of the cannula and thus provides an increased central bore area. It is preferred that the harvesting head demonstrate a rounded, for example, "egg shaped" contour, as demonstrated in FIGS. 1, 2 and 3 so as to assist the instrument in effecting the above and below-described blunt dissection of tissue about the vessel to be harvested. The tubular control segment 23 is located contiguous and proximal to the harvesting head and is discussed in further detail, below. Portions of the outer walls of both the harvesting head 12 and tubular control segment 23 (portions of said sections located upon a superior surface 7 of the cannula opposite the inferior surface of the cannula 77) are comprised of a sliding operation arm 9. The sliding operation arm 9, as discussed above, is slidably affixed to a superior portion of the harvesting head and tubular control segment so as to enable fore/aft motion of the arm. Aft motion of the arm 3, motion of the arm towards to proximal terminus 10 of the cannula, (the "open" position) forms an opening in the outer walls of the harvesting head—the branch vessel capture notches 22 and 24. Fore motion of the sliding arm 5, motion of the arm towards the distal terminus of the cannula allows opposing walls of the capture notches to approximate each other (the "closed" position) and enables, in certain preferred embodiments, the cauterization (in certain preferred embodiments, application of clips/coils) and sectioning of branch arteries also discussed below. Therefore, a distal portion of the sliding operation arm completes the outer wall of superior portion of the harvesting head when the device is in the closed configuration.

In the first preferred embodiment of the present invention illustrated in FIGS. 1–5, the distal terminus 8 of the cannula is open so as to form a distal aperture 9 which is contiguous with the central bore 6. A main vessel alignment slot 20 penetrating through the outer wall 4 of the cannula arises at its distal terminus from and communicates with the distal aperture 9 of the cannula. Thus both the distal bore and alignment slot provide access to the central bore within the cannula. In the first preferred embodiment of the present invention, the main vessel alignment slot 20 is not aligned with the longitudinal axis of the cannula, but lies at an angular relationship with said axis. Utilizing a skewed main vessel alignment slot further enhances the ability of the harvesting head to capture a vessel to be harvested. For example, if the main vessel alignment slot is aligned with the longitudinal axis of the cannula, the vessel might be easily displaced from the harvesting head as the cannula progressed along a vessel and was thus brought into alignment with the vessel.

In the first preferred embodiment, the alignment slot extends from the distal aperture, proximally along the outer wall of the harvesting cannula and terminates at a point 21 along the superior outer wall of the harvesting head formed by the sliding operation arm and in close proximity to the proximal terminus of the harvesting head 25. Thus the main vessel alignment slot comprises an opening of the outer wall of the cannula extending from the distal aperture along the outer wall of the harvesting head and terminates at a distal portion of the sliding operation arm 9.

In preferred embodiment illustrated in FIGS. 1–5, two branch vessel capture notches 22 and 24 are formed by the aforementioned aft motion of the sliding operation arm 9. More specifically, aft motion 3 of the arm opens a channel in the outer wall of a distal portion of the harvesting head running in a generally circumferential direction about the longitudinal axis of the cannula which communicates with both the central bore as well as the main vessel alignment slot. The notches thus formed are especially useful in the capture and severance of branch arteries. More specifically, when the sliding operation arm is urged in an aft direction, a channel—and, in regard to the first preferred embodiment of the present invention, 2 channels are formed—so as to provide a pair of branch vessel capture notches 22 and 24. These notches are advantageously provided with means therewithin for both cauterizing and severing branch vessels from a main vessel to be harvested. In the first preferred embodiment of the present invention illustrated in FIGS. 1–5, electro-surgery points 30, 32, 34 and 36 located upon the proximal walls of the branch vessel capture notches are oppositely charged (ground or active) as compared to electro-surgery contact points 38, 40, 42 and 44 positioned within and upon the opposing distal notch walls. Therefore, when, as described below, branch vessels are maneuvered into the capture notches, forward movement of the sliding operation arm provides direct contact between the electrodes (contact points) and branch vessels. Activation of an electro-surgery unit connected to the aforementioned operating points, allows the surgeon to seal of such vessels in to locations—one location more proximal to the main vessel and one location more distal. Alternatively, the aforementioned contacts may, by means of forward motion of the sliding operation arm, be energized without need to independently activate an electro or radio cautery unit for each successive cautery application. In the first preferred embodiment of the present invention, a cutting blade 46 and 48 located upon the notch walls and positioned between adjacent radio or electro-surgery points allows the cannula to sever the branch vessels between the cauterization points. Operation of the cutting blade may be controlled by the closure (fore movement) of the sliding operation arm, or a separate control rod may be utilized to actuate the blades.

The harvesting cannula of the present invention includes a means for capturing, retaining and manipulating a vessel to be harvested once the vessel has been introduced into the central bore of the harvesting head through the main vessel alignment slot. The vessel capture and manipulation means may be advantageously comprised of a control rod positioned and retained within the tubular control segment or the sliding control arm of the cannula. Such control rods include, at a distal terminus, a vessel capturing configuration designed to engage and hold a vessel for manipulation while still allowing proximal and distal movement of the device along the vessel. At a proximal terminus, the control rod includes a control means 52 so as to allow a surgeon to rotate, extend and retracting the vessel capturing configuration. For example, while the central portion of the control rod lies in general alignment with the longitudinal axis of the cannula, the distal terminus—the vessel capturing configuration—, may comprise a 90 degree bend in the rod thereafter presenting a "V" or "U" shaped opening of sufficient size so as to engage and provide manipulation of the vessel. In such embodiments, rotation of the control rod allows an operator to alter the position of the main vessel within the harvesting head so as to facilitate capture of branch vessels within the branch vessel capture notches.

In the first preferred embodiment of the present invention illustrated in FIGS. 1–5, control rod 50 includes dial 52 for rotation, extension and retraction of the rod and a "pig tail" vessel capturing configuration 54 on the distal terminus thereof. Rotation of the control rod 50 allows capture and manipulation of the vessel—and the side branches attached thereto—in regard to movement of the vessel in superior 1, inferior 3 and lateral directions. Such control of the main vessel and resultant control of branch vessels, facilitates placement of branches into the capture notches for cauterization and removal.

Figure 6:
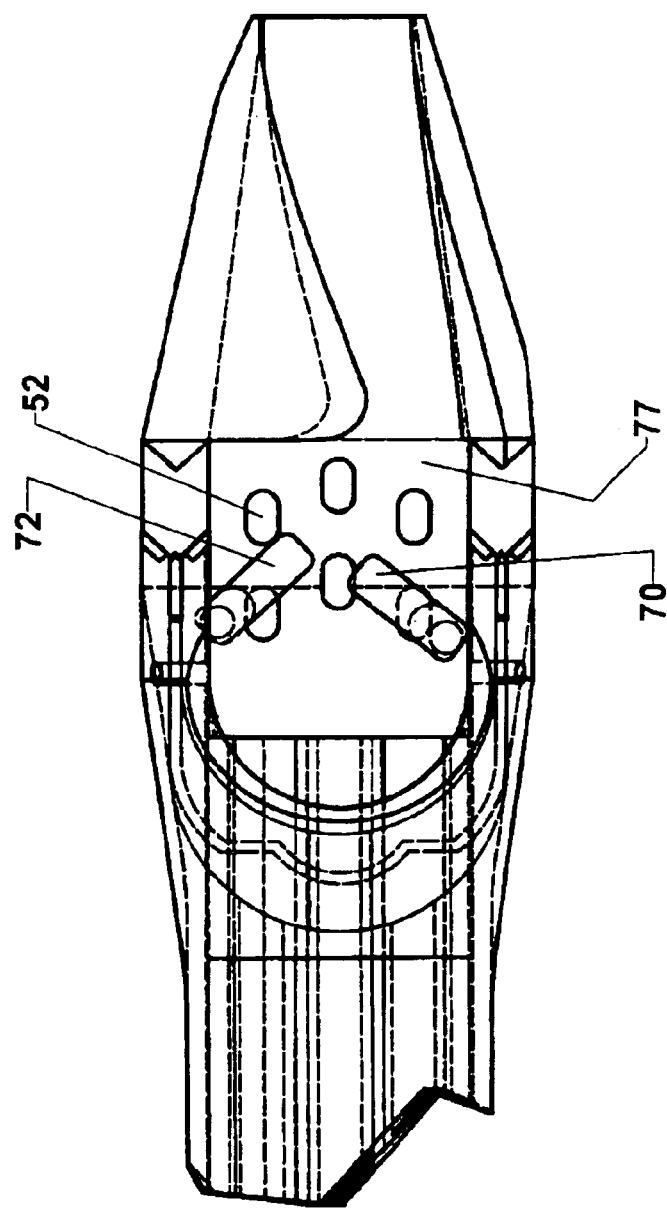
FIG. 6 is a top view of a portion of an alternate preferred embodiment of the present invention.

In a first alternative preferred embodiment of the present invention (illustrated in FIG. 6), a main vessel retention means comprises retention gates 70 and 72. The retention gates, shown in a "closed" position, are utilized to ensure retention of the vessel to be harvested within the central bore of the harvesting head. In addition, the location of the gates, just distal to the proximal terminus of the main alignment slot, applies a strategic downward force upon the main vessel (towards the inferior surface of the cannula 77). The downward biasing force is the result of i. the traction force already applied to the vessel due to its intact position , both proximally and distally within the circulatory conduit; and ii. the opposing retentive force applied to the vessel to be harvested by the gates just prior to exit of the vessel from the proximal termini of the main alignment slot. As the cannula is advanced, proximally along a vessel to be harvested, the biasing force tends to urge branch vessels into the capture notches located, as discussed above, in close proximity with the capture gates. In the first preferred embodiment, the main vessel capture/manipulation means, e.g., the control rod with pig tail also provide similar downward biasing force and the resulting facilitation of branch vessel notch capture. However, embodiments incorporating the capture/manipulation means demonstrate the added utility of allowing increased control of vessel position.

In the first preferred embodiment of the present invention, the tubular control segment, provides a conduit and advantageously includes multiple channels for an endoscopic camera, operating light, vessel control rod, irrigation and aspiration. . The inferior surface 77 of the outer wall of the cannula may advantageously include a plurality of perforations 52 allowing for irrigation and aspiration of both the operative site (within the harvesting head) as well as irrigation and aspiration of the field about the cannula. It has now been discovered, as discussed in further detail above, that by including a gaseous stream of $CO_2$ within the irrigant stream, the viability of the endothelium of vessels to be harvested may be greatly improved .

Figure 4:
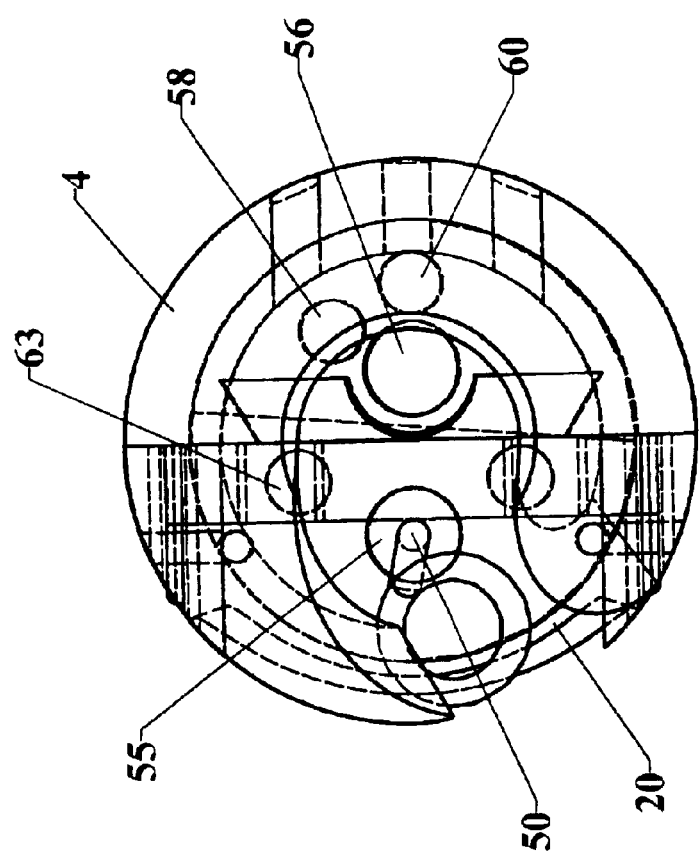
FIG. 4 is a cross sectional view of the preferred embodiment illustrated in FIG. 1
Figure 5:
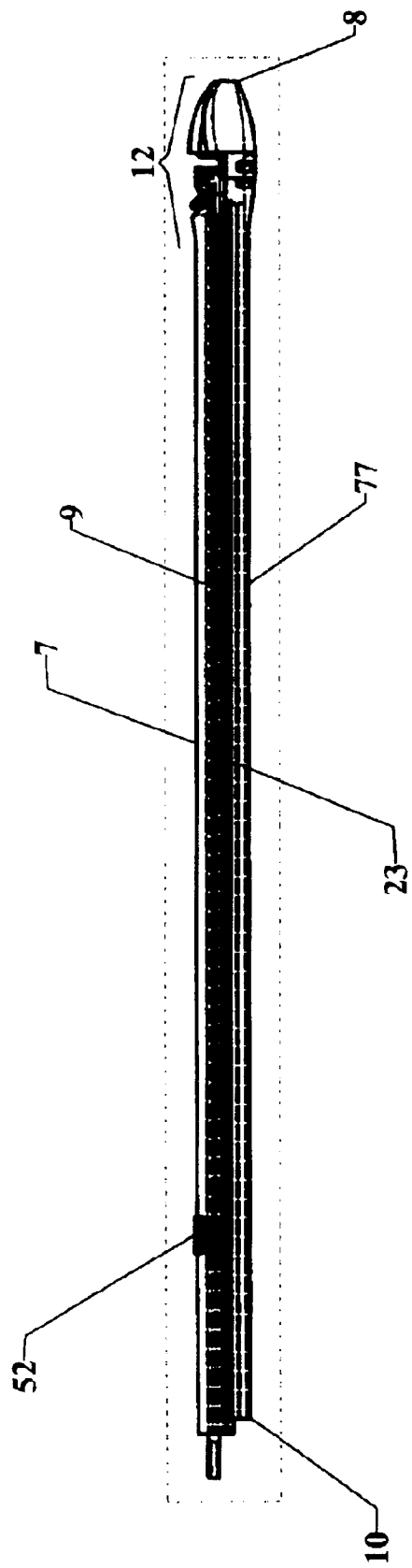
FIG. 5 is a lateral view illustrating the entire length of the embodiment shown in FIG. 1.

FIG. 4 is a cross sectional view of the first preferred embodiment. Control rod channel 55 provides a conduit and mounting means for control rod 50. In addition, fiber optic endoscopic camera 56 and light 63 are located adjacent to irrigation channel 58 which provides both irrigation of the operative field as well as a cleansing stream so as to keep the lens of the camera free of debris. Aspiration channel 60 provides a conduit for the removal of irrigant, blood and other debris from the operative field.

It is highly advantageous to position the endoscopic camera lens within the tubular control segment, just proximal to, and directed towards the central bore of the harvesting head. Alternatively, such cameras may be placed within the sliding control arm. As stated above, the relatively large central bore of the harvesting cannula provides a wide operative field and excellent visualization. It is still further advantageous to utilize a lens with a sufficient field width so as to provide and generate an image providing a view of the central bore of the harvesting head, the branch vessel capture notches and the main vessel alignment slot. Such positioning and field performance of the endoscopic camera and lens will therefore enable a surgeon the view 1. the vessel to be harvested; 2. the position of the vessel to be harvested during vessel introduction into the harvesting head (during the rotation, extension and retraction of the cannula by the surgeon as he or she attempts to position the vessel within the main vessel alignment slot); 3. manipulation of the control rod and vessel capture/manipulation means (e.g. "pig tail"); 4. manipulation of branch vessels, after capture by the capture control means, so as to position same within the branch vessel capture notches; 5. positioning the branch vessels within the branch vessel capture notches so as to align said vessels with the cautery and cutting means; and 6. cauterization (or, in certain preferred embodiments, the application of clips and/or coils) and severing of branch vessels.

In practicing the method of the first preferred embodiment of the present invention, a vessel to be harvested is first identified. For example, it may be highly desirable to harvest the radial artery for use in bypass surgery. Therefore, after properly anesthetizing the patient, a skin incision is made at a point adjacent to the most distal extent of the vessel to be harvested after preparing the surgical site in the usual manner and after application of the usual disinfecting agents. Thereafter, a blunt dissection is carried out proximally, along the vessel sufficient so as to provide an ample operative field about the vessel. For this purpose, conventional surgical instruments may be utilized. However, the tapered "egg shaped" harvesting head of the embodiments of the present invention illustrated in the figures may also be utilized to provide such dissection. For this purpose, the harvesting cannula may be provided with a removable (such as "screw on" or "snap on") domed shaped cap for occlusion of the distal aperture during this initial procedural step. After sufficient blunt dissection is performed, the vessel, such as, for example, the radial artery, remains intact without any severance of the vessel at either the proximal or distal extent of the graft. The vessel is purposefully allowed to remain intact in this manner so as to take advantage of the traction and stabilization provided by the connection of the vessel—at both ends of the graft—, to the remainder of its course. The cannula is then positioned by the surgeon, utilizing the endoscopic camera for guidance, so as to urge the most distal extent of the graft to be harvested—the main vessel—into the main vessel alignment slot 20. After positioning the main vessel within the slot, the surgeon then utilizes the main vessel capture and manipulation means to engage and capture the vessel. For example, the surgeon may utilize a control means to rotate, extend and retract the "pig tail" shaped distal terminus of the control rod so as to engage the main vessel.

As the cannula is advanced toward the proximal extent of the graft to be harvested, the main vessel passes through the distal aperture, into the central bore of the harvesting head, through the capturing configuration of the control rod (e.g. "pig tail") and then exits the central bore of the harvesting head at the proximal terminus of the alignment slot. Thereafter, the vessel passes, substantially parallel to the long axis of the cannula against the devices outer surface. Upon encountering lateral vessels (observed through the camera) the surgeon utilizes a dial 50 or other control means to rotate extend and retract the control rod so as to manipulate the vessel to be harvested so as to position lateral branch vessels within the capture notches 22 and 24. The control rod may be utilized in conjunction with manipulation of the entire cannula, or by itself, in order to position the branch vessels in such a manner as they are aligned with hemostatic and severing means. The surgeon may then advance the sliding operation arm forward, in a fore direction, so as to provide contact of opposing (ground and active) electro-surgical tips with each vessel on either side of the cutting means. Upon contact with the branch vessels, current is applied to the branch vessels so as to cauterize same at two points lateral to the point where the vessel is to be severed. Activation of the electro-surgery unit providing the cauterizing wave form may be provided by sliding contacts within the cannula that close upon forward motion of the sliding operation arm completing a circuit or may optionally be provided by a manually operated control switch mounted upon or separate from the tubular control segment.

After cauterization of a branch vessel, a cutting means, such as, for example, a cutting electro-surgical current, laser, harmonic cutter or sharpened metal blade, located between the cauterization points, is used to transect the branch vessel. In the first preferred embodiment of the present invention illustrated in FIGS. 1–5, sharpened steel edge 46 and 48, located upon the notch walls and positioned between adjacent electro-surgery points, allows the cannula to sever the branch vessels between the cauterization points. Operation of the cutting blade may be controlled by the closure (fore movement) of the sliding operation arm, or a separate control rod may be utilized to actuate the blades.

The terms and expressions which have been employed in the foregoing specification and in the abstract are used therein as terms of description and not limitation, and there is no intention, in the use of such terms and expressions, of excluding equivalents of the features shown and described or portions thereof, it being recognized that the scope of the invention is defined and limited only by the following claims.

I claim:

1. A blood vessel harvesting cannula having outer walls defining a central bore therewithin, a proximal terminus, a distal terminus and a longitudinal axis, said cannula being comprised of:

a harvesting head, a tubular control segment and a sliding operation arm, wherein the sliding operation arm is slidably affixed to a superior portion of both the control segment and the harvesting head thereby enabling fore and aft movement of the sliding operation arm relative to the proximal and distal terminus of the cannula;

a main vessel alignment slot penetrating through a portion of the outer walls of the harvesting head and sliding operation arm, said slot beginning at the distal terminus of said cannula and ending within the outer wall of the sliding operation arm, said main vessel alignment slot communicating with the central bore of the harvesting cannula;

at least one branch vessel capture notch located between a portion of the outer walls of the cannula comprising a distal terminus of the sliding operation arm and a superior portion of the harvesting head adjacent thereto, wherein the at least one branch vessel capture notch is circumferentially aligned relative to the longitudinal axis of the cannula and communicates with the central bore thereof and wherein the branch vessel capture notch is lateral to and communicates with the main vessel alignment slot, and wherein the capture notch includes a means there within for severing branch vessels from a blood vessel to be harvested; and a main vessel retention means for retaining a vessel to be harvested within the central bore of the harvesting head.

2. The harvesting cannula of claim 1 wherein said harvesting head demonstrates an elliptical shape.

3. The blood vessel harvesting device of claim 1 wherein said main vessel alignment slot is configured in an angular, non-parallel relation relative to the longitudinal axis of the device.

4. The blood vessel harvesting device of claim 1 wherein said cannula includes a distal aperture.

5. The blood vessel harvesting device of claim 4 wherein said cannula further comprises a removable cap so as to enhance use of said device in blunt dissection.

6. The blood vessel harvesting device of claim 1 wherein the main vessel alignment slot provides a longitudinal opening within the outer wall of said cannula equal to or greater than a width of a vessel to be harvested by said device.

7. The harvesting cannula of claim 1 wherein said cannula includes two branch vessel capture notches.

8. The harvesting cannula of claim 1 wherein said main vessel retention means is configured to apply a biasing force to said vessel so as to assist placement of branch vessels arising therefrom into said at least one branch vessel capture notch.

9. The harvesting cannula of claim 1 wherein said at least one branch vessel capture notch includes a means for effecting hemostasis of said branch vessels.

10. The harvesting cannula of claim 9 wherein said means of hemostasis is selected from the group consisting of electro cautery, radio cautery, surgical clips and surgical coils.

11. The harvesting cannula of claim 10 wherein said electro surgery and radio surgery are configured to utilize unipolar current.

12. The harvesting cannula of claim 10 wherein said electro surgery and radio surgery are configured to utilize bipolar current.

13. The harvesting cannula of claim 9 wherein each of said at least one branch vessel capture notch includes at least one severing means operably mounted within said notch and disposed between two hemostatic means.

14. The harvesting cannula of claim 13 wherein said severing means is selected from the group consisting of a cold steel blade, a harmonically operated blade, an electro surgery tip, a radio surgery tip and a laser.

15. The harvesting cannula of claim 14 wherein said electro surgery tip and radio surgery tip are configured to utilize bipolar current.

16. The harvesting cannula of claim 14 wherein said electro surgery tip and radio surgery tip are configured to utilize unipolar current.

17. The harvesting cannula of claim 13 wherein said hemostatic means are selected from the group consisting of electro cautery, radio cautery, surgical clips and surgical coils.

18. The harvesting cannula of claim 17 wherein said electro surgery and radio surgery are configured to utilize unipolar current.

19. The harvesting cannula of claim 17 wherein said electro surgery and radio surgery are configured to utilize bipolar current.

20. The harvesting cannula of claim 1 wherein said means for severing branch vessels is selected from the group consisting of a cold steel blade, a harmonically operated blade, an electro surgery tip, a radio surgery tip and a laser.

21. The harvesting cannula of claim 20 wherein said electro surgery tip and radio surgery tip are configured to utilize bipolar current.

22. The harvesting cannula of claim 20 wherein said electro surgery tip and radio surgery tip are configured to utilize unipolar current.

23. The harvesting cannula of claim 1 further comprising a main vessel retention and manipulation means thereby enabling said device to both retain and manipulate the position of the vessel within the central bore of the cannula.

24. The harvesting cannula of claim 23 wherein said main vessel capture and manipulation means comprises a control rod.

25. The harvesting cannula of claim 24 wherein the control rod is generally aligned with the longitudinal axis of the cannula and includes, at a proximal terminus thereof, a means for controlling rod operation and at a distal terminus, a vessel engaging configuration enabling said rod to engage and manipulate a vessel's position within the central bore of the cannula.

26. The harvesting cannula of claim 25 wherein said vessel engaging configuration is selected from the group consisting of a "V" shaped, "L" shaped and coil shaped distal terminus.

27. The harvesting cannula of claim 1 wherein the main vessel retention means comprises retention gates.

28. The harvesting cannula of claim 1 wherein said device further comprises a remote camera positioned within said cannula so as to enable observation of capture and manipulation of a vessel to be harvested as within the cannula as well as the manipulation and severing of branch vessels therefrom.

29. The harvesting cannula of claim 1 wherein said cannula further comprises a means of irrigating an operative field about said vessel to be harvested.

30. The harvesting cannula of claim 29 wherein said irrigation means is especially configured and adapted to delivers a saline solution to the operative field.

31. The harvesting cannula of claim 29 wherein said irrigating means is especially configured and adapted to deliver an agent for enhancing the production of nitric oxide by endothelial cells of the vessel to be harvested.

32. The harvesting cannula of claim 31 wherein the agent for enhancing the production of nitric oxide is $CO_2$.

33. The harvesting cannula of claim 32 wherein said irrigating means is configured and adapted to deliver a flow of about 2 liters/minute to about 4 liters/minute of $CO_2$ to the operative field.

34. The harvesting cannula of claim 1 wherein said device also includes an aspiration means.

35. The blood vessel harvesting device of claim 34 wherein said cannula includes a plurality of aspiration and irrigation holes penetrating the outer walls of said cannula.

36. A blood vessel harvesting cannula having outer walls defining a central bore therewithin, a proximal terminus, a distal terminus and a longitudinal axis, said cannula being comprised of:

a harvesting head, a tubular control segment and a sliding operation arm, wherein the sliding operation arm is slidably affixed to a superior portion of both the control segment and the harvesting head thereby enabling fore and aft movement of the sliding operation arm relative to the proximal and distal terminus of the cannula, wherein a distal aperture is located at the distal terminus of said cannula and wherein the harvesting head demonstrates a greater diameter relative to other segments of the cannula;

a main vessel alignment slot penetrating through outer walls of the harvesting head and sliding operation arm, said slot beginning at the distal terminus of said cannula and ending within the outer wall of the sliding operation arm, said main vessel alignment slot communicating with the central bore of the harvesting cannula and wherein said main vessel alignment slot is configured in an angular, non-parallel relation relative to the longitudinal axis of the device;

two branch vessel capture notches located between outer walls of the cannula comprising a distal terminus of the sliding operation arm and a superior portion of the harvesting head adjacent thereto, wherein the branch vessel capture notches are circumferentially aligned in relation to the longitudinal axis of the cannula communicate with the central bore thereof and are lateral to and continuous with the main vessel alignment slot, wherein each of the capture notches include a branch vessel severing means operably mounted and disposed between two hemostatic means; and a main vessel retention and manipulation means for retaining a vessel to be harvested within the main vessel alignment slot and positioning lateral branch vessels within the branch vessel capture notches.

37. The harvesting cannula of claim 36 wherein said means of hemostasis is selected from the group consisting of electro cautery, radio cautery, surgical clips and surgical coils.

38. The harvesting cannula of claim 37 wherein said electro surgery and radio surgery are configured to utilize unipolar current.

39. The harvesting cannula of claim 37 wherein said electro surgery and radio surgery are configured to utilize bipolar current.

40. The harvesting cannula of claim 36 wherein said means for severing branch vessels is selected from the group consisting of a cold steel blade, a harmonically operated blade, an electro surgery tip, a radio surgery tip and a laser.

41. The harvesting cannula of claim 40 wherein said electro surgery tip and radio surgery tip are configured to utilize bipolar current.

42. The harvesting cannula of claim 40 wherein said electro surgery tip and radio surgery tip are configured to utilize unipolar current.

43. The harvesting cannula of claim 36 wherein said main vessel capture and manipulation means comprises a control rod.

44. The harvesting cannula of claim 43 wherein the control rod is generally aligned with the longitudinal axis of the cannula and includes, at a proximal terminus thereof, a means for controlling rod operation and at a distal terminus, a vessel engaging configuration enabling said rod to engage and manipulate a vessel's position within the central bore of the cannula.

45. The harvesting cannula of claim 44 wherein said vessel engaging configuration is selected from the group consisting of a "V" shaped, "L" shaped and coil shaped distal terminus.

46. The harvesting cannula of claim 36 wherein said device further comprises a remote camera positioned within said cannula so as to enable observation of capture and manipulation of a vessel to be harvested as within the cannula as well as the manipulation and severing of branch vessels therefrom.

47. The harvesting cannula of claim 36 wherein said cannula further comprises a means of irrigating an operative field about said vessel to be harvested.

48. The harvesting cannula of claim 47 wherein said irrigation means is especially configured and adapted to delivers a saline solution to the operative field.

49. The harvesting cannula of claim 47 wherein said irrigating means is especially configured and adapted to deliver an agent for enhancing the production of nitric oxide by endothelial cells of the vessel to be harvested.

50. The harvesting cannula of claim 49 wherein the agent for enhancing the production of nitric oxide is $CO_2$.

51. The harvesting cannula of claim 50 wherein said irrigating means is configured and adapted to deliver a flow of about 2 liters/minute to about 4 liters/minute of $CO_2$ to the operative field.

52. The harvesting cannula of claim 36 wherein said device also includes an aspiration means.

53. The blood vessel harvesting device of claim 52 wherein said cannula includes a plurality of aspiration and irrigation holes penetrating the outer walls of said cannula.

* * * * *